(12) United States Patent
Feng

(10) Patent No.: US 11,913,927 B2
(45) Date of Patent: Feb. 27, 2024

(54) INTELLIGENT NITROGEN-OXYGEN SENSOR AND DETECTION METHOD THEREOF

(71) Applicant: CHANGZHOU LAMBDA ELECTRONIC., LTD, Jiangsu (CN)

(72) Inventor: Jiangtao Feng, Jiangsu (CN)

(73) Assignee: CHANGZHOU LAMBDA ELECTRONIC., LTD, Jiangsu (CN)

( * ) Notice: Subject to any disclaimer, the term of this patent is extended or adjusted under 35 U.S.C. 154(b) by 862 days.

(21) Appl. No.: 16/980,379

(22) PCT Filed: Jan. 22, 2019

(86) PCT No.: PCT/CN2019/072623
§ 371 (c)(1),
(2) Date: Sep. 12, 2020

(87) PCT Pub. No.: WO2019/154062
PCT Pub. Date: Aug. 15, 2019

(65) Prior Publication Data
US 2021/0239669 A1    Aug. 5, 2021

(30) Foreign Application Priority Data

Feb. 11, 2018 (CN) .......................... 201810139637.7

(51) Int. Cl.
*G01N 27/27* (2006.01)
*G01N 27/407* (2006.01)
(Continued)

(52) U.S. Cl.
CPC ......... *G01N 33/0037* (2013.01); *F01N 3/208* (2013.01); *F01N 3/32* (2013.01);
(Continued)

(58) Field of Classification Search
CPC .. G01N 27/27; G01N 27/4071; G01N 27/419; F01N 2560/026
See application file for complete search history.

(56) References Cited

U.S. PATENT DOCUMENTS

2016/0061768 A1* 3/2016 Nakasone ............ G01N 27/301
                                                                    204/412
2017/0276636 A1* 9/2017 Tominaga .......... G01N 27/4067

OTHER PUBLICATIONS

CN 204924863 machine translation. (Year: 2015).*
(Continued)

*Primary Examiner* — Caitlyn Mingyun Sun

(57) ABSTRACT

An intelligent nitrogen-oxygen sensor and a detection method thereof are disclosed. The sensor includes an induction chip. The induction chip includes a substrate unit, a printing function unit and a closed structural unit. The substrate unit includes an upper zirconia substrate (1), a middle zirconia substrate (2) and a lower zirconia substrate (3). The printing function unit includes a common external electrode (11), a main pump internal electrode (12), an auxiliary pump internal electrode (13), a mixed potential sensitive electrode (31), a measurement pump internal electrode (32), a reference air electrode (33), a first insulation coating layer (41), a second insulation coating layer (42), a heating circuit (43) and eight electrode contact points. The closed structural unit includes a first measurement cavity (21), a second measurement cavity (22) and a reference air passage (23).

4 Claims, 1 Drawing Sheet

(51) Int. Cl.
*G01N 27/419* (2006.01)
*G01N 33/00* (2006.01)
*F01N 3/20* (2006.01)
*F01N 3/32* (2006.01)

(52) U.S. Cl.
CPC ......... *G01N 27/27* (2013.01); *G01N 27/4071* (2013.01); *G01N 27/419* (2013.01); *F01N 2560/026* (2013.01)

(56) References Cited

OTHER PUBLICATIONS

DE 102016208506 machine translation. (Year: 2016).*
J. Park, Sensing behavior and mechanism of mixed potential NOx sensors using NiO, NiO(+YSZ) and CuO oxide electrodes; Sensor and Actuators B: Chemical, 2009 (135), p. 516-23. (Year: 2009).*

* cited by examiner

INTELLIGENT NITROGEN-OXYGEN SENSOR AND DETECTION METHOD THEREOF

CROSS REFERENCE OF RELATED APPLICATION

This is a U.S. National Stage under 35 U.S.C 371 of the International Application PCT/CN2019/072623, filed, which claims priority under 35 U.S.C. 119(a-d) to CN 201810139637.7, filed Feb. 11, 2018.

BACKGROUND OF THE PRESENT INVENTION

Field of Invention

The present invention relates to a sensor, and more particularly to an intelligent nitrogen-oxygen sensor and a detection method thereof.

Description of Related Arts

A large amount of nitrogen oxides are produced when a diesel engine burns at high temperature under oxygen-rich conditions. In the process of treating exhaust gas of the diesel engine, the selective catalytic reaction (SCR) method is widely used since it is able to efficiently treat NOX. In this method, urea is added as a reactive substance. Therefore, it is necessary to respectively add nitrogen-oxygen sensors before and after the SCR process to accurately measure the concentration of NOX, so that the exhaust gas aftertreatment system achieves the functions of precise control and on-board diagnosis. At present, the only nitrogen-oxygen sensor for mass applications is based on the current-type working principle, which determines and detects the total amount of $NO_X$ on the basis of the increase in oxygen content after $NO_X$ decomposition. When he exhaust gas with NO as the main component is measured, its accuracy is guaranteed to be stable, but when the exhaust gas with $NO_2$ as the main component or with $NO_2$ occupying a considerable proportion is measured, the measured value is inaccurate because the amount of oxygen in $NO_2$ is twice that of NO.

Since diesel oxidation catalyst (DOC) is generally not installed in the post-treatment of China IV emissions, $NO_2$ in the exhaust gas before the SCR accounts for about 10% of the total $NO_X$, and $NO_2$ fully participates in the fast response with $NH_3$ in the SCR, so that there is basically no $NO_2$ after the SCR. Therefore, the measurement of existing nitrogen-oxygen sensors is not inaccurate due to $NO_2$ in $NO_X$. However, after the emissions have been upgraded to China VI emissions, it is almost necessary to install the DOC in the post-treatment of diesel engines. The $NO_2$ in the exhaust gas before the SCR accounts for nearly or even more than 50% of the total $NO_X$, which causes that $NO_X$ may be all $NO_2$ after the SCR, and especially when the China IV emission regulation has the very low $NO_X$ limit value, existing current-type nitrogen-oxygen sensors are unable to meet the requirement of measurement accuracy. Therefore, there is an urgent need for a nitrogen-oxygen sensor with high measurement accuracy for NO and $NO_2$.

SUMMARY OF THE PRESENT INVENTION

An object of the present invention is to overcome above deficiencies, so that an induction chip for an intelligent nitrogen-oxygen sensor is provided.

To solve the above technical problem, the present invention provides a technical solution as follows. An induction chip for an intelligent nitrogen-oxygen sensor comprises a substrate unit, a printing function unit and a closed structural unit, wherein:

the substrate unit comprises an upper zirconia substrate, a middle zirconia substrate and a lower zirconia substrate;

the printing function unit comprises a common external electrode, a main pump internal electrode, an auxiliary pump internal electrode, a mixed potential sensitive electrode, a measurement pump internal electrode, a reference air electrode, a first insulation coating layer, a second insulation coating layer, a heating circuit and eight electrode contact points;

the closed structural unit comprises a first measurement cavity, a second measurement cavity and a reference air passage;

the common external electrode is connected with a common electrode contact point through a lead wire, and is printed on an upper end surface of the upper zirconia substrate; the main pump internal electrode, the auxiliary pump internal electrode and lead wires thereof are printed on a lower end surface of the upper zirconia substrate; the main pump internal electrode and the auxiliary pump internal electrode are respectively connected with a first electrode contact point and a second electrode contact point, both of which are printed on the upper end surface of the upper zirconia substrate, through the lead wires via through-holes in the upper zirconia substrate; the mixed potential sensitive electrode and the measurement pump internal electrode are printed on an upper end surface of the lower zirconia substrate, and are respectively connected with a third electrode contact point and a fourth electrode contact point both of which are located at two sides of the lower zirconia substrate through lead wires; the reference air electrode and a lead wire thereof are printed on the upper end surface of the lower zirconia substrate, and the reference air electrode is connected with a fifth electrode contact point which is located at a lower end surface of the lower zirconia substrate via a through-hole in the lower zirconia substrate; the first insulation coating layer and the second insulation coating layer are directly printed on the lower end surface of the lower zirconia substrate, and wrap the heating circuit; a length of the second insulation coating layer is smaller than a length of the first insulation coating layer such that the fifth electrode contact point, a sixth electrode contact point and a seventh electrode contact point are exposed to air; the first measurement cavity, the second measurement cavity and the reference air passage are provided on the middle zirconia substrate through punching process, and a first diffusion barrier layer and a second diffusion barrier layer are provided on the middle zirconia substrate.

Preferably, the mixed potential sensitive electrode is provided within the first measurement cavity.

Preferably, the first diffusion barrier layer is provided at a front end of the first measurement cavity, the second diffusion barrier layer is provided at a rear end of the first measurement cavity.

Preferably, the mixed potential sensitive electrode is made from NiO and $ZrO_2$ with a mass ratio in a range from 2:1 to 1:1.

Preferably, the intelligent nitrogen-oxygen sensor further comprises: a main pump unit VP0 for connecting the common external electrode with the main pump internal electrode, an auxiliary pump unit VP1 for connecting the common external electrode with the auxiliary pump internal electrode, a measurement pump unit VP2 for connecting the common external electrode with the measurement pump internal electrode, a first measurement cavity oxygen concentration difference battery unit V0 for connecting the main pump internal electrode with the reference air electrode, a second measurement cavity oxygen concentration difference battery unit V1 for connecting the reference air electrode with the auxiliary pump internal electrode, a measurement pump catalytic decomposition electrode oxygen concentration difference battery unit V2 for connecting the reference air electrode with the measurement pump internal electrode, a mixed potential measurement unit VR for connecting the main pump internal electrode with the mixed potential sensitive electrode.

Also, the present invention provides a detection method of the intelligent nitrogen-oxygen sensor, the detection method comprising steps of:

(1) the exhaust gas entering the first measurement cavity through the first diffusion barrier layer, the main pump unit VP0 maintaining an oxygen concentration $V_0$ of the first measurement cavity to a certain constant value through feedback adjustment, oxidizing HC, CO and $H_2$ in the exhaust gas, ensuring a concentration of NO and $NO_2$ is stable, wherein a main pump limit current IP0 produced by the main pump unit is in direct proportion to an air-fuel ratio of the exhaust gas;

(2) under a condition that the oxygen concentration in the first measurement cavity is fixed, detecting a potential difference Vr between the mixed potential sensitive electrode and the main pump internal electrode, and obtaining a relative content ratio of NO to $NO_2$, wherein Vr=NO/$NO_2$;

(3) gas in the first measurement cavity diffusing into the second measurement cavity through the second diffusion barrier layer, maintaining an oxygen concentration $V_1$ of the second measurement cavity through the auxiliary pump unit VP1 at a lower constant value, converting $NO_2$ into NO, and determining an amount of oxygen that enters the second measurement cavity through an auxiliary pump limit current IP1 produced by the auxiliary pump unit;

(4) decreasing an oxygen concentration around a catalytic decomposition electrode in the second measurement cavity through the measurement pump unit VP2 to $V_2$, completing decomposing NO into $N_2$ and $O_2$ through the measurement pump internal electrode, pumping the decomposed $O_2$ through the measurement pump unit, and forming a measurement pump current IP2, wherein the measurement pump current IP2 is in direct proportion to a total concentration of NOx, here IP2=NOx; and (5) calculating a ratio of the measurement pump current IP2 and the auxiliary pump limit current IP1, obtaining the total concentration of $NO_X$, and calculating concentrations of NO and $NO_2$ based on the potential difference Vr of the mixed potential detection unit, respectively.

Beneficial effects of the present invention are as follows. This intelligent nitrogen-oxygen sensor is able to not only accurately measure the total amount of $NO_X$ in the exhaust gas through the current-type working principle, but also detect the ratio of NO to $NO_2$ in the exhaust gas through the mixed potential characteristic, so that the concentrations of NO and $NO_2$ in the exhaust gas are able to be accurately calculated, respectively.

BRIEF DESCRIPTION OF THE DRAWINGS

The present invention is further explained with accompanying drawings and embodiments as follows.

Figure 1:
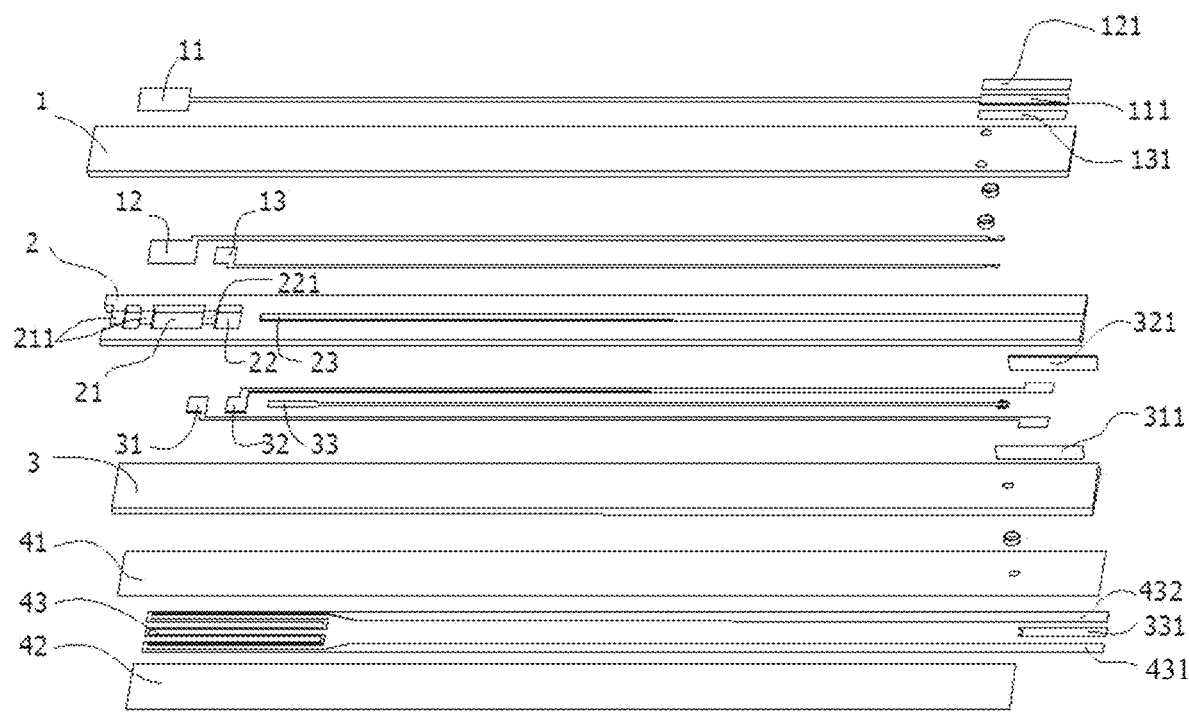
FIG. 1 is a structurally schematic view of an induction chip for an intelligent nitrogen-oxygen sensor provided by the present invention.

In the drawings, 1: upper zirconia substrate; 11: common external electrode; 12: main pump internal electrode; 13: auxiliary pump internal electrode; 111: common electrode contact point; 121: first electrode contact point; 131: second electrode contact point; 2: middle zirconia substrate; 21: first measurement cavity; 22: second measurement cavity; 23: reference air passage; 211: first diffusion barrier layer; 221: second diffusion barrier layer; 3: lower zirconia substrate; 31: mixed potential sensitive electrode; 32: measurement pump internal electrode; 33: reference air electrode; 311: third electrode contact point; 321: fourth electrode contact point; 331: fifth electrode contact point; 41: first insulation coating layer; 42: second insulation coating layer; 43: heating circuit; 431: sixth electrode contact point; 432: seventh electrode contact point.

DETAILED DESCRIPTION OF THE PREFERRED EMBODIMENT

Figure 2:
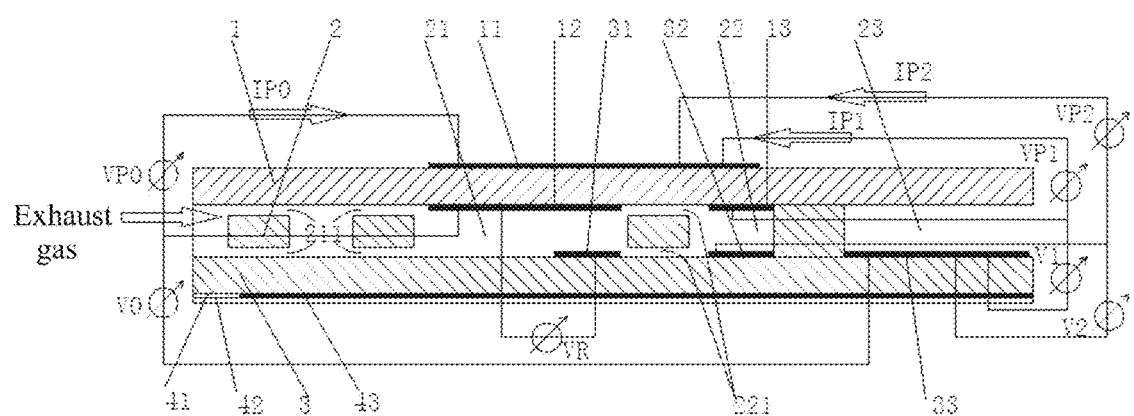
FIG. 2 is a structurally schematic view of the intelligent nitrogen-oxygen sensor provided by the present invention.

FIG. 1 shows an induction chip for an intelligent nitrogen-oxygen sensor, FIG. 2 shows an intelligent nitrogen-oxygen sensor with mixed potential and current signal characteristics, which is able to not only accurately measure the total amount of $NO_X$ in the exhaust gas through the current-type working principle, but also detect the ratio of NO to $NO_2$ in the exhaust gas through the mixed potential characteristic, so that the concentrations of NO and $NO_2$ in the exhaust gas are accurately calculated, respectively.

The nitrogen-oxygen sensor provided by the present invention comprises three substrates all of which define a first measurement cavity, a second measurement cavity, a reference air passage and a heating unit. The sensor is special in that in addition to a main pump unit, an auxiliary pump unit and a measurement pump unit, a measurement part comprises a mixed potential detection unit, and there are six electrodes in the measurement part; the heating unit comprises two electrodes. The mixed potential detection unit, which is located within the first measurement cavity, comprises a sensitive electrode which takes NiO as a catalytic material and a main pump unit internal electrode as a reference electrode. A diffusion barrier layer is provided between the first measurement cavity and an exterior, and another diffusion barrier layer is provided between the first measurement cavity and the second measurement cavity.

Referring to FIG. 1, the induction chip comprises a substrate unit, a printing function unit and a closed structural unit, wherein the substrate unit comprises an upper zirconia substrate 1, a middle zirconia substrate 2 and a lower zirconia substrate 3; the printing function unit comprises a common external electrode 11, a main pump internal electrode 12, an auxiliary pump internal electrode 13, a mixed potential sensitive electrode 31, a measurement pump internal electrode 32, a reference air electrode 33, a first insulation coating layer 41, a second insulation coating layer 42, a heating circuit 43 and eight electrode contact points; the closed structural unit comprises a first measurement cavity 21, a second measurement cavity 22 and a reference air passage 23, wherein the common external electrode 11 is connected with a common electrode contact point 111 through a lead wire, and is printed on an upper end surface of the upper zirconia substrate 1; the main pump internal electrode 12, the auxiliary pump internal electrode 13 and lead wires thereof are printed on a lower end surface of the upper zirconia substrate 1; the main pump internal electrode 12 and the auxiliary pump internal electrode 13 are respectively connected with a first electrode contact point 121 and a second electrode contact point 131, both of which are printed on the upper end surface of the upper zirconia substrate 1, through the lead wires via through-holes in the upper zirconia substrate 1; the mixed potential sensitive electrode 31 and the measurement pump internal electrode 32 are printed on an upper end surface of the lower zirconia substrate 3, and are respectively connected with a third electrode contact point 311 and a fourth electrode contact point 321 both of which are located at two sides of the lower zirconia substrate 3 through lead wires; the reference air electrode 33 and a lead wire thereof are printed on the upper end surface of the lower zirconia substrate 3, and the reference air electrode 33 is connected with a fifth electrode contact point 331 which is located at a lower end surface of the lower zirconia substrate 3 via a through-hole in the lower zirconia substrate 3; the first insulation coating layer 41 and the second insulation coating layer 42 are directly printed on the lower end surface of the lower zirconia substrate 3, and wrap the heating circuit 43 which is connected with the first insulation coating layer 41 and the second insulation coating layer 42 through printed connection; a length of the second insulation coating layer 42 is less than a length of the first insulation coating layer 41, such that the fifth electrode contact point 331, a sixth electrode contact point 431 and a seventh electrode contact point 432 are exposed to air; the first measurement cavity 21, the second measurement cavity 22 and the reference air passage 23 are provided on the middle zirconia substrate 2 through punching process, and a first diffusion barrier layer 211 and a second diffusion barrier layer 221 are also provided on the middle zirconia substrate 2.

The common external electrode 11, the main pump internal electrode 12, the auxiliary pump internal electrode 13, the measurement pump internal electrode 32, the reference air electrode 33 and the mixed potential sensitive electrode 31 are functional signal measurement electrodes.

The mixed potential sensitive electrode 31 is provided within the first measurement cavity 21.

The first diffusion barrier layer 211 is provided at a front end of the first measurement cavity 21, the second diffusion barrier layer 221 is provided at a rear end of the first measurement cavity 21.

As shown in FIG. 2, an intelligent nitrogen-oxygen sensor is illustrated, which comprises the induction chip shown in FIG. 1, a main pump unit VP0 for connecting the common external electrode 11 with the main pump internal electrode 12, an auxiliary pump unit VP1 for connecting the common external electrode 11 with the auxiliary pump internal electrode 13, a measurement pump unit VP2 for connecting the common external electrode 11 with the measurement pump internal electrode 32, a first measurement cavity oxygen concentration difference battery unit V0 for connecting the main pump internal electrode 12 with the reference air electrode 33, a second measurement cavity oxygen concentration difference battery unit $V_1$ for connecting the reference air electrode 33 with the auxiliary pump internal electrode 13, a measurement pump catalytic decomposition electrode oxygen concentration difference battery unit $V_2$ for connecting the reference air electrode 33 with the measurement pump internal electrode 32, a mixed potential measurement unit VR for connecting the main pump internal electrode 12 with the mixed potential sensitive electrode 31.

The six measurement electrodes of the nitrogen-oxygen sensor are respectively a main pump external electrode (which is also an auxiliary pump external electrode and a measurement pump external electrode), the main pump internal electrode (which is also a mixed potential reference electrode), the mixed potential sensitive electrode, the auxiliary pump internal electrode, the measurement pump internal electrode and the reference air electrode. The heating unit comprises two electrodes. The temperature of the heating unit is adjusted and controlled on a basis of an internal resistance of the first measurement cavity oxygen concentration difference battery unit between the main pump internal electrode and the reference air electrode, and then is stably maintained at around 800° C. Another characteristic of the sensor during the process of actual work and control is that: the concentrations of the first measurement cavity and the second measurement cavity are constant, so that the closed-loop control logic of the signal controller is simpler, and the accuracy of the individual signal and measurement value of each sensor is calibrated and calculated through the main pump limit current, the auxiliary pump limit current and the measurement pump current.

Moreover, the mixed potential sensitive electrode 31 is made from NiO and $ZrO_2$ with a mass ratio in a range from 2:1 to 1:1.

Referring to FIG. 2, when the sensor works, exhaust gas of an automobile is detected by a method comprising steps of:

(1) the exhaust gas entering the first measurement cavity 21 through the first diffusion barrier layer 211, the main pump unit VP0 maintaining an oxygen concentration $V_0$ of the first measurement cavity 21 to a certain constant value through feedback adjustment, oxidizing HC, CO and $H_2$ in the exhaust gas, ensuring a concentration of NO and $NO_2$ is stable, wherein a main pump limit current IP0 produced by the main pump unit is in direct proportion to an air-fuel ratio of the exhaust gas;

(2) under a condition that the oxygen concentration in the first measurement cavity 21 is fixed, detecting a potential difference Vr between the mixed potential sensitive electrode 31 and the main pump internal electrode 12, and obtaining a relative content ratio of NO to $NO_2$, wherein Vr=NO/$NO_2$;

(3) gas in the first measurement cavity 21 diffusing into the second measurement cavity 22 through the second diffusion barrier layer 221, maintaining an oxygen concentration $V_1$ of the second measurement cavity 22 through the auxiliary pump unit VP1 at a lower constant value, converting $NO_2$ into NO, and determining an amount of oxygen that enters the second measurement cavity 22 through an auxiliary pump limit current IP1 produced by the auxiliary pump unit;

(4) decreasing an oxygen concentration around a catalytic decomposition electrode in the second measurement cavity 22 through the measurement pump unit VP2 to $V_2$, completing decomposing NO into $N_2$ and $O_2$ through the measurement pump internal electrode 32, pumping the decomposed $O_2$ through the measurement pump unit, and forming a measurement pump current IP2, wherein the measurement pump current IP2 is in direct proportion to a total concentration of $NO_x$, here IP2=NOx; and (5) calculating a ratio of the measurement pump current IP2 and the auxiliary pump limit current IP1, obtaining the total concentration of $NO_x$, and calculating concentrations of NO and $NO_2$ based on the potential difference Vr of the mixed potential detection unit, respectively.

The oxygen concentration $V_0$ of the first measurement cavity and the oxygen concentration $V_1$ of the second measurement cavity are maintained at a constant value, so that the closed-loop control logic of the signal controller is simpler, and the accuracy of the individual signal and measurement value of each sensor is calibrated and calculated through the auxiliary pump limit current IP1, the measurement pump limit current IP2 and the potential difference Vr. The main pump limit current IP0 is able to accurately measure the air-fuel ratio through calibration.

The technical route for detecting NOx concentration by the mixed potential is to use metal oxide MOS as the sensitive electrode, $ZrO_2$ as the oxygen ion conductor, and noble electrode Pt as the reference electrode, nitrogen oxides perform a catalytic reaction at the sensitive electrode to affect the transmission of oxygen ions, thereby forming a response potential. Specifically, NOx diffuses through the sensitive electrode layer into the three-phase interface, NOx and $O_2$ perform different electrochemical redox reactions at the three-phase interface of the sensitive electrode (SE) and the reference electrode (RE).

RE(Pt) side:

(for NO) $O_2 + 4e^- \rightarrow 2O^{2-}$ (1)

(for $NO_2$) $2O^{2-} \rightarrow O_2 + 4e^-$ (2)

SE(MOS) side:

(for NO) $NO + O^{2-} \rightarrow NO_2 + 2e^-$ (3)

(for $NO_2$) $NO_2 + 2e^- \rightarrow NO + O^{2-}$ (4)

There is NOx adsorption and reaction at the SE end, but Pt-RE has no such effect. Therefore, even under the same gas, a potential is still generated between the SE and the RE. However, the NO reaction consumes oxygen ions to provide electrons, the $NO_2$ reaction is just the opposite. Therefore, when the mixed gas of NO and $NO_2$ responds, there will be an offset. According to this response principle, the potential difference between the sensitive electrode and the reference electrode in a mixed gas is able to reflect the ratio of NO to $NO_2$ to a certain extent.

The intelligent nitrogen-oxygen sensor provided by the present invention is able to accurately detect the concentrations of NO and $NO_2$, respectively, and has a mixed potential signal and a current signal. However, compared with the traditional pure current-type sensor, the number of electrodes and the arrangement of the pin position of the induction element provided by the present invention are unchanged, so that the package of the overall device is more compatible in package, and is easy to be mass produced and popularized.

What is claimed is:

1. An intelligent nitrogen-oxygen sensor comprising an induction chip, wherein the induction chip comprises a substrate unit, a printing function unit and a closed structural unit, wherein:

the substrate unit comprises an upper zirconia substrate (1), a middle zirconia substrate (2) and a lower zirconia substrate (3);

the printing function unit comprises a common external electrode (11), a main pump internal electrode (12), an auxiliary pump internal electrode (13), a mixed potential sensitive electrode (31), a measurement pump internal electrode (32), a reference air electrode (33), a first insulation coating layer (41), a second insulation coating layer (42), a heating circuit (43) and eight electrode contact points;

the closed structural unit comprises a first measurement cavity (21), a second measurement cavity (22) and a reference air passage (23);

the common external electrode (11) is connected with a common electrode contact point (111) through a lead wire, and is printed on an upper end surface of the upper zirconia substrate (1);

the main pump internal electrode (12), the auxiliary pump internal electrode (13) and lead wires thereof are printed on a lower end surface of the upper zirconia substrate (1);

the main pump internal electrode (12) and the auxiliary pump internal electrode (13) are respectively connected with a first electrode contact point (121) and a second electrode contact point (131), both of which are printed on the upper end surface of the upper zirconia substrate (1), through the lead wires via through-holes in the upper zirconia substrate (1);

the mixed potential sensitive electrode (31) and the measurement pump internal electrode (32) are printed on an upper end surface of the lower zirconia substrate (3), and are respectively connected with a third electrode contact point (311) and a fourth electrode contact point (321) both of which are located at two sides of the lower zirconia substrate (3) through lead wires;

the reference air electrode (33) and a lead wire thereof are printed on the upper end surface of the lower zirconia substrate (3), and the reference air electrode (33) is connected with a fifth electrode contact point (331) which is located at a lower end surface of the lower zirconia substrate (3) via a through-hole in the lower zirconia substrate (3);

the first insulation coating layer (41) and the second insulation coating layer (42) are printed on the lower end surface of the lower zirconia substrate (3), and wrap the heating circuit (43);

a length of the second insulation coating layer (42) is smaller than a length of the first insulation coating layer (41), such that the fifth electrode contact point (331), a sixth electrode contact point (431) and a seventh electrode contact point (432) are exposed to air;

the first measurement cavity (21), the second measurement cavity (22) and the reference air passage (23) are provided on the middle zirconia substrate (2) through punching process, and a first diffusion barrier layer (211) and a second diffusion barrier layer (221) are provided on the middle zirconia substrate (2);

the intelligent nitrogen-oxygen sensor further comprises a main pump unit VP0 for connecting the common external electrode (11) with the main pump internal electrode (12), an auxiliary pump unit VP1 for connecting the common external electrode (11) with the auxiliary pump internal electrode (13), a measurement pump unit VP2 for connecting the common external electrode (11) with the measurement pump internal electrode (32), a first measurement cavity oxygen concentration difference battery unit V0 for connecting the main pump internal electrode (12) with the reference air electrode (33), a second measurement cavity oxygen concentration difference battery unit V1 for connecting the reference air electrode (33) with the auxiliary pump internal electrode (13), a measurement pump catalytic decomposition electrode oxygen concentration difference battery unit V2 for connecting the reference air electrode (33) with the measurement pump internal electrode (32), a mixed potential measurement unit VR for connecting the main pump internal electrode (12) with the mixed potential sensitive electrode (31).

2. The intelligent nitrogen-oxygen sensor according to claim 1, wherein the mixed potential sensitive electrode (31) is provided within the first measurement cavity (21).

3. The intelligent nitrogen-oxygen sensor according to claim 1, wherein the first diffusion barrier layer (211) is provided at a front end of the first measurement cavity (21), the second diffusion barrier layer (221) is provided at a rear end of the first measurement cavity (21).

4. The intelligent nitrogen-oxygen sensor according to claim 1, wherein the mixed potential sensitive electrode (31) is made from NiO and $ZrO_2$ with a mass ratio in a range from 2:1 to 1:1.

* * * * *